United States Patent [19]
Kalish

[11] 4,176,664
[45] Dec. 4, 1979

[54] IMPREGNATED BANDAGE

[76] Inventor: Stanley Kalish, 2727 De Anza Rd., M-22, San Diego, Calif. 92109

[21] Appl. No.: 885,620

[22] Filed: Mar. 13, 1978

[51] Int. Cl.$^2$ ............................................. A61L 15/00
[52] U.S. Cl. ..................................... 128/156; 128/268
[58] Field of Search ................. 128/156, 155, 82, 268, 128/290 R, 169-171

[56] References Cited
U.S. PATENT DOCUMENTS

| | | | |
|---|---|---|---|
| 1,911,291 | 5/1933 | Reynolds | 128/156 X |
| 2,145,755 | 1/1939 | Dickson | 128/156 |
| 2,469,064 | 5/1949 | Campbell | 128/156 |
| 2,572,641 | 10/1951 | Manley | 128/156 |
| 2,721,550 | 10/1955 | Banff | 128/156 |
| 3,256,881 | 6/1966 | Stenvall | 128/156 |
| 4,053,053 | 10/1977 | Tumangday | 128/155 X |

Primary Examiner—John D. Yasko

[57] ABSTRACT

An impregnated bandage having a backing strip with an adhesive coating on one side. A layer of or patch of absorbent material positioned in the approximate center from the ends of the backing strip. An impregnated layer of gauze adapted to contact the wound positioned above the absorbent layer. The impregnated bandage includes protective strips for protecting the adhesive surfaces until immediately prior to use and for separating the impregnated layer and the absorbent material. The protective strips are removed by a pulling movement applied to the ends of the protective strip prior to use of the bandage.

22 Claims, 7 Drawing Figures

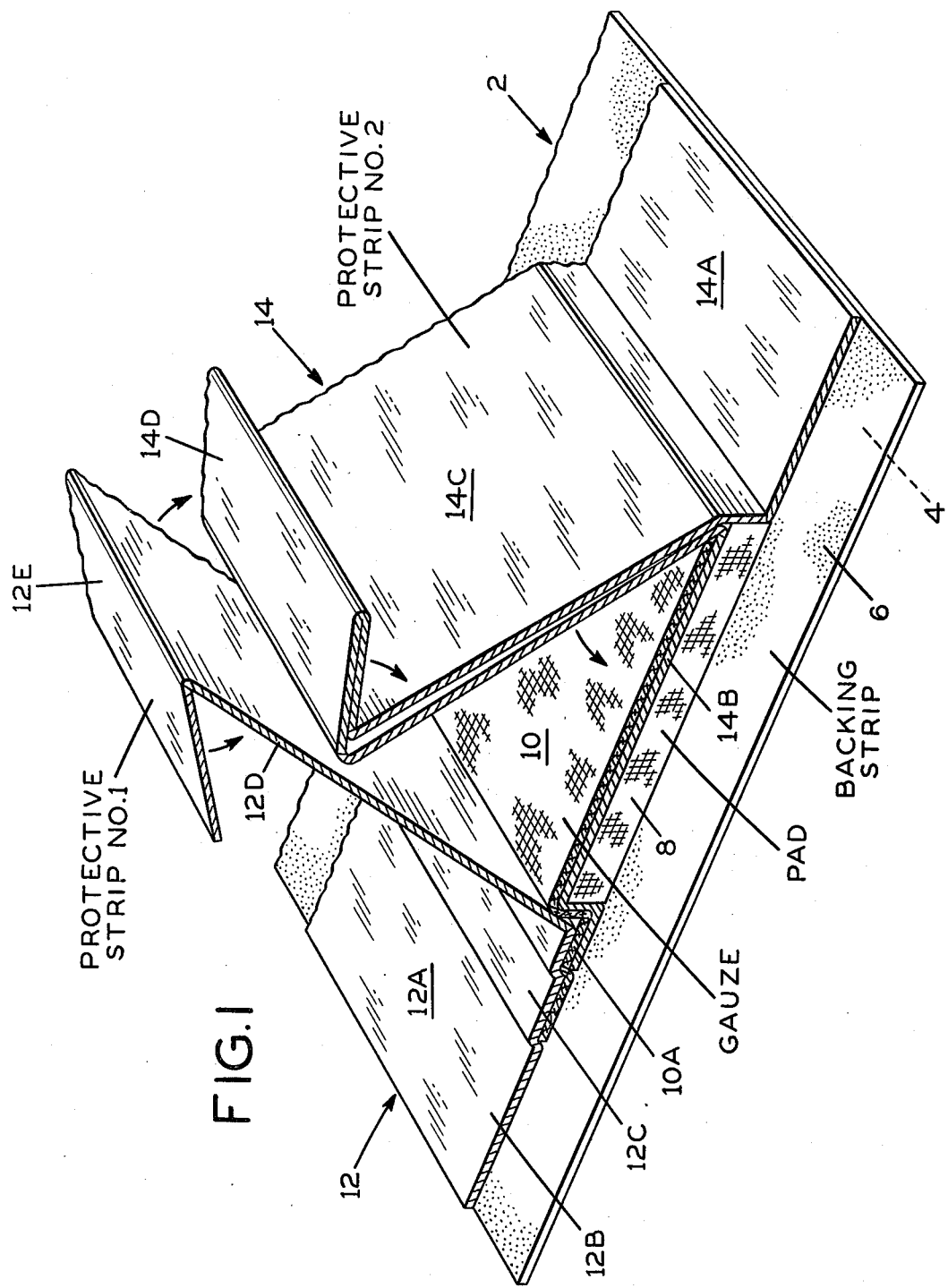

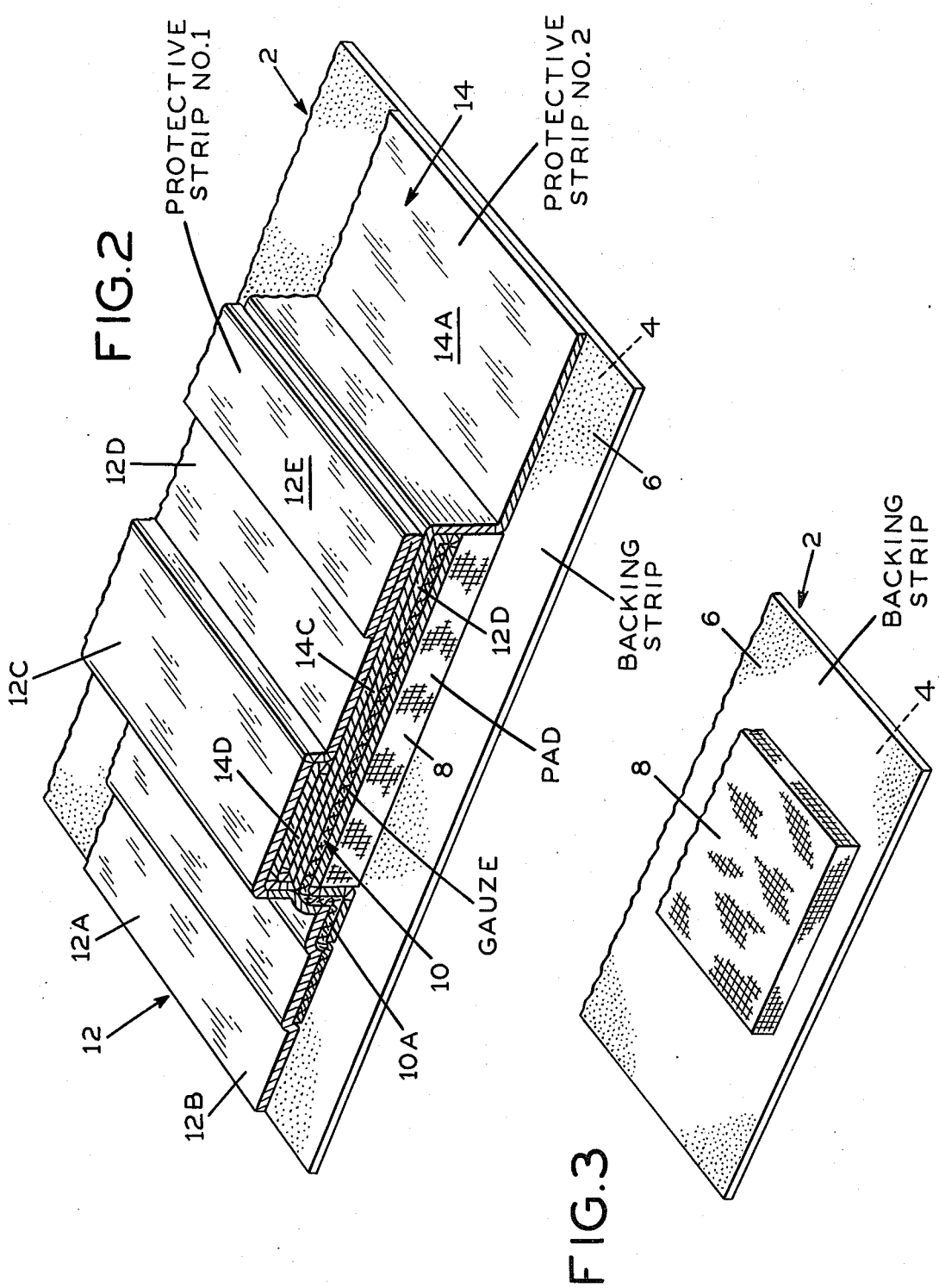

IMPREGNATED BANDAGE

BACKGROUND OF THE INVENTION

This invention relates to an impregnated bandage, a method of assembling the same and a method of applying the same.

The use of ointment impregnated dressings for application to wounds is well established in the prior art practices. Depending upon the ointment used as the impregnant, virtually any desired effect in medical treatment of the wound can be obtained. However, to be effective, the impregnated dressing must be covered by a layer of absorbent material, and be held in place by an outer wrap or binder. Thus, it has been found that to be effective the dressing must have three (3) layers. The impregnated layer is required in order to provide such medical treatment as may be desired. However, the impregnated layer cannot successfully be used without an absorbent layer since an absorbent layer is required to prevent maceration.

The absorbent layer is required to absorb secretions from the wound in order to prevent maceration, to protect the wound by cushioning it against external traumatic forces, to help prevent the impregnated dressing from sticking to the wound, and to avoid staining of clothing and bed linen by the impregnant.

The outer wrap or binder is required to hold the various components in functioning contact with each other and with the wound, and to keep the complete dressing in proper position with the wound. Unless an adhesive strip is used as the outer wrap or binder, a circumferential wrapping must be applied which may make the total dressing unnecessarily bulky, and carries with it the possible danger of constricting the wound if edema, or swelling, develops.

At the present time where such dressings are required it is necessary for the attending physician or nurse to construct such a dressing. This is difficult and inconvenient and frequently results in a bulky, overlarge and sometimes contaminated dressing.

Since such a construction has not been available, prior to the present invention, it has not been possible to keep on hand previously prepared and pre-packaged dressings incorporating all three layers. Therefore, it has been necessary to construct each dressing individually from the individual components. As noted, in the hands of inexperienced or untrained personnel this frequently results in improper, poorly constructed and possibly contaminated dressings.

Previously, the drawback to pre-packaging three-layer dressings involving the use of an impregnated contact dressing, an absorbent layer, and a binder of adhesive tape is that during sterilization and storage the ointment tended to wick into the absorbent material, thereby removing it from contact with the wound.

Another problem is that with an impregnated layer it is necessary to keep the impregnated layer separated from the absorbent layer to prevent wicking or seepage of the impregnant into the absorbent layer which would destroy or diminish the absorbent qualities of that layer. Additionally, it is necessary to keep the impregnant separate from the adhesive since many of the impregnants will destroy or diminish the adhesive qualities of the adhesive strip.

However, a need exists for a previously prepared and pre-packaged, sterile dressing which includes an impregnated gauze strip, an absorbent layer and an adhesive strip. This would avoid the need to construct such a dressing for each individual wound. Such a construction even in the hands of unskilled personnel could be easily applied without risking contamination of the dressing. It would be particularly useful in hospitals, physicians' offices, first-aid rooms and, most importantly, in the home.

There are, of course, available in the prior art a number of different bandages which include a backing strip having an adhesive surface on one side, a portion of which is attached to an absorbent gauze member. In some commercial embodiments protective strips are provided which can be peeled away from the adhesive surfaces prior to application. This type of dressing is referred to herein as the protected bandage type.

The main problem with the protected bandage type is that they do not permit the wound to heal because they do not include an impregnated layer. Indeed, after prolonged use of such a bandage maceration develops under the bandage, thereby preventing the wound from healing. These bandages do little more than temporaily protect the wound from further damage from external sources.

OBJECTS

In view of the foregoing it is an object of this invention to provide an impregnated bandage structure.

Another object of this invention is to provide a three-layer dressing which can cover a wound and assist in the healing process.

Another object of this invention is to provide a dressing having an impregnated layer, an absorbent layer in engagement with the impregnated layer and an adhesive means for attaching said dressing to the body of the patient.

A still further object of this invention is to provide a layered dressing which is sterilized, pre-packaged having, at least, an adhesive layer, an absorbent layer and an impregnated layer, with a protective layer or strip between the absorbent layer and an impregnated layer which prevents contact between the impregnated layer and absorbent layers until the dressing is ready for use.

A still further object of this invention is to provide a bandage-like structure having an adhesive layer, an absorbent layer and an impregnated layer wherein protective strip means are provided which cover the adhesive surfaces and separate the impregnated layer and the absorbent layer until immediately prior to application to a wound.

Another object of this invention is to provide an impregnated dressing adapted to be adhesively attached having means for preventing damage to the dressing prior to use including during sterilization.

Another object of this invention is to provide a new and improved method for assembling a three-layer impregnated dressing.

Another object of this invention is to provide a new and improved method for applying an impregnated dressing to a wound.

Another object of this invention is to provide a method of assembling an impregnated bandage comprising placing an absorbent pad on the adhesive side of a backing strip, placing an impregnated gauze strip with respect to the absorbent pad and applying protective strips between the absorbent pad and impregnated gauze and to the adhesive surface of the backing strip.

Another object of this invention is to provide a method of assembling an impregnated bandage comprising the steps of applying an absorbent pad to the approximate center of a backing strip having an adhesive surface and applying an impregnated gauze strip and protective strips so that the absorbent pad and impregnated gauze strip are separate and the adhesive surfaces of the backing strip are protected prior to application of the bandage to the wound.

Additional objects and advantages of the invention will be set forth in the description which follows and, in part, will be obvious from the description, the objects and advantages being realized and obtained by means of the instrumentation, parts, methods, apparatus and procedures particularly pointed out in the appended claims.

BRIEF DESCRIPTION OF THE INVENTION

Briefly described, the invention comprises a backing strip having an adhesive coating on one side. Positioned in the approximate center from the ends of the strip is a layer or patch of an absorbent material. Positioned above the absorbent layer is an impregnated layer of gauze or the like which is adapted to be in contact with a wound.

The invention may further include protective strips for protecting the adhesive surfaces until immediately prior to use and for serving as a protective barrier between the impregnated layer and the absorbent layer. The protective strips referred to herein are also sometimes referred to as a release paper and by a pulling movement applied to the end of the protective strips, the adhesive surfaces are uncovered or activated and the impregnated layer and the absorbent layer come into face-to-face contact.

As embodied, there are first and second protective strips. The first protective strip includes a first leg which engages one of the adhesive surfaces of the backing strip until the bandage is ready for use. The first protective strip includes a second leg having at the terminal end a gripping means. The second leg in the non-use position overlies the second protective strip. The second protective strip, as embodied herein, consists of a first leg means which engages the other of the backing strip adhesive surfaces and a second leg means which is positioned between the absorbent pad and the impregnated gauze strip so as to prevent the impregnant from wicking into the absorbent pad. The second protective strip includes a third or common leg means which in the folded or non-use position overlies the upper surface of the impregnated gauze. The second protective strip also includes a gripping means at the terminal end of the third leg which is engaged by hand and pulled when the impregnated bandage is ready for use.

In use, the impregnated bandage is applied as follows. The impregnated bandage is removed from its sterilized package and moved to a position adjacent to the wound to which it is to be applied.

The free ends or gripping portions of the protective strips are then grasped by hand and pulled in opposite directions so that the impregnated bandage is first exposed and then placed in light contact with the wound. At the same time the entire impregnated bandage is moved into increased contact with the wound. As force is applied to the gripping ends of the protective strips, the legs of the protective strips engaging the adhesive surfaces of the backing strip are gradually peeled from the adhesive surfaces and these adhesive surfaces are gradually adhered to the body adjacent to the wound. In this manner the adhesive surfaces gradually engage the body adjacent the wound. At the same time that the legs of the protective strips are being peeled from the adhesive surfaces the second leg of the second protective strip which was originally positioned between the impregnated gauze layer and the absorbent pad is gradually pulled and removed from its position between these layers. With a slight rubbing action, the adhesive surface can be firmly engaged with that portion of the body adjacent to the wound and at the same time the impregnated layer will engage the wound.

Briefly described, the invention further includes a method of assembling an impregnated bandage of the type described above. As embodied, this invention comprises the steps of placing a layer of absorbent material in engagement with the adhesive surface of a backing strip at the approximate midpoint of the backing strip. The legs of release papers are placed in engagement with the adhesive surface of the backing strip adjacent to the absorbent material. One of the legs on one of the release papers is placed in face-to-face superimposed relationship with the upper surface of the absorbent material. A sheet of gauze is placed in face-to-face superimposed relationship with the upper surface of the release paper. The free legs of the release papers are folded so as to cover the upper surface of the impregnated gauze and so that the free ends of the release papers are in position to be manually engaged and separated so as to release the release papers from engagement with the adhesive surfaces of the backing strip and to withdraw the leg of the release paper which is sandwiched between the absorbent pad and the impregnated member so that the impregnated bandage can be applied to a wound.

The invention consists of the novel parts, steps, construction and improvements shown and described.

The accompanying drawings which are incorporated in and constitute part of this specification illustrate an embodiment of the invention and together with the description serve to explain the principles of the invention.

OF THE DRAWINGS

FIG. 1 is a perspective view of an impregnated bandage of this invention which is partially assembled.

FIG. 2 is a perspective view of the impregnated bandage of this invention fully assembled.

FIG. 3 is a perspective view of the first of a series of diagrammatic assembly drawings.

DETAILED DESCRIPTION OF THE INVENTION

Figure 4:
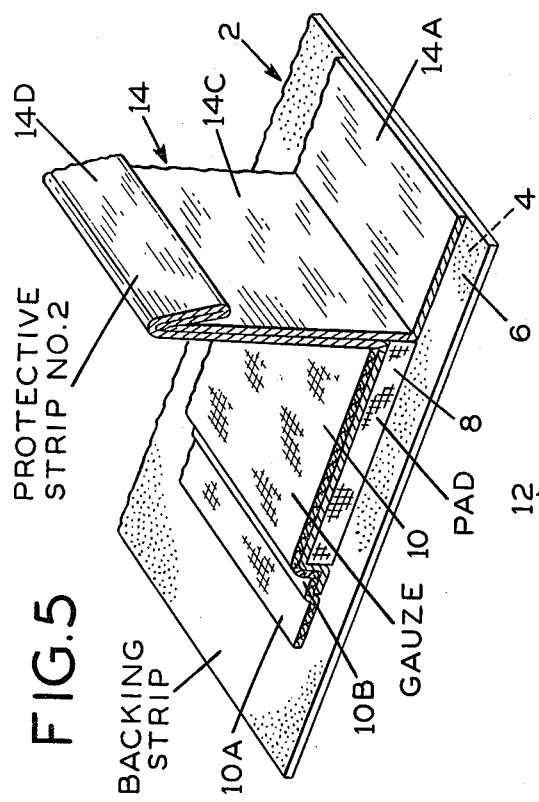
FIG. 4 is a drawing of the invention similar to FIG. 3 with protective strip No. 2 added.

As referred to in this application certain terms mentioned herein should be construed as follows:

1. Contact or Impregnated Layer—That portion of a dressing which comes into superimposed, face-to-face contact with a wound. It may consist of one or more layers of material capable of following the contours of the wound. Although medical experience indicates the preferred material for a contact dressing to be fine mesh, absorbent, cotton gauze, it does not exclude other fabrics, woven or non-woven, synthetic or natural, absorbent or non-absorbent, wet or dry. This layer is at some point in the process impregnated with an impregnant as described below.

2. Absorbent Layer—That portion of a dressing which is between the contact layer and the backing strip. It may consist of one or more layers of any absorbent material, and may be woven or non-woven, synthetic or natural. Experience indicates that the absorbent layer should be relatively thick and capable of affording adequate capacity to absorb wound secretions, and to serve as a protective cushion against additional trauma. It may be referred to in this application as absorbent layer, absorbent filler, or absorbent pad.

3. Backing Strip—As discussed in this application the outer wrap or binder may consist of any material, woven or non-woven, synthetic or natural, porous or non-porius, perforated or non-perforated, elastic or non-elastic, which has an adhesive coating on one side of the material.

4. Impregnant—As discussed in the application, the term impregnant means any ointment, unguent or salve, whether water soluble or non-water soluble, hydrophylic or hydrophobic, inert or containing active medicaments in an oil or wax base, an oil emulsion base, or a liquid base.

5. Protective Strips—The protective strips must be able to withstand the sterilization temperatures and be impervious to oil. It could be made of many materials such as aluminum foil, polypropylene or treated paper. It must be capable of being folded and/or manipulated for the purposes intended.

Referring to FIG. 1 the impregnated bandage of the invention is shown in partially assembled condition.

As shown in the drawings, backing strip means is provided for the impregnated bandage. The backing strip 2 is the type having a non-adhesive side 4 and an adhesive side 6. As will be seen the backing strip is the element to which the remainder of the impregnated bandage structure is attached. The adhesive portion 6 of the backing strip can adhere firmly to the other bandage portions and to the human body with the application of slight pressure. One type of adhesive backing is known as Micropore 3M surgical tape, but other adhesive backings on plastic or coated paper, plain paper or elastic tapes, etc. may be employed. The adhesive tape must, among other things, be able to withstand the chosen sterilization process.

The invention includes means for absorbing blood and other fluids coming from the wound. As embodied, this means comprises an absorbent pad 8 which is somewhat thicker than the ordinary bandage. There are several materials available on the market for this purpose folded to give a multi-ply pad of one inch in width. In one embodiment, a non-woven absorbent filler called WEBRIL R2853 made by Kendall Mfg. Co. of suitable thickness was used.

The next level of the impregnated bandage is a sheet of gauze 10. The sheet is constructed of a dry absorbent cotton gauze of preferably 44/36 mesh although other mesh sizes may be appropriate. The gauze would be approximately one-quarter (¼) inches wider than the size of the absorbent pad, and preferably selvage-edged. The width could be varied from other sizes of dressings.

The dry absorbent gauze at some time during the manufacturing process is impregnated with an impregnant. The impregnant, preferably, should be available in a form which will permit continuous, controlled application to the dry absorbent gauze. Depending on the purpose of the impregnated bandage different types of substances can be used as the impregnant.

Thus, for example, where the impregnant is to serve a therapeutic or medicinal purpose it is preferred that the impregnant be bismuth tribromophenate in a bland oil emulsion. Such a substance is commercially known as XEROFLO which imparts a medicinal odor and color to the impregnated bandage. This substance is suggested since it is hydrophilic and will enhance drainage of the wound secretion into the absorbent pad. In some instances an ointment which is hydrophobic such as petrolatum may be desirable. Other substances may be used as the impregnant depending upon the function or result desired to be obtained.

The invention further includes protective means for shielding the adhesive surfaces of the backing strip and for separating the absorbent pad and impregnated gauze until immediately prior to use.

As embodied this protective means includes first 12 and second 14 protective strips. These strips whose detailed function is explained later can be made of any suitable material which is impervious to oil, which will withstand the sterilization process and which can be folded and/or manipulated into the positions indicated below and shown in the drawings. Many materials are available which might possibly be used for the protective strips, including aluminum foil, polypropylene film or paper which has been coated so as to make it impervious to oil.

In the preferred embodiment of this invention the protective strip or release paper is made of forty (40) pound paper coated with polypropylene.

In accordance with this invention the protective strips or release papers comprise at least a pair of strips designated herein as the first and second strips. The first protective strip 12 has several leg portions as hereinafter described.

The first protective strip 12 includes a first leg means 12A having portions 12B and 12C. The portion 12B covers and protects the adhesive surface on one side of the bandage. There is another portion 12C which is in superimposed relationship with a portion of the impregnated gauze 10A which extends beyond the absorbent pad 10. Until removed this leg of the protective strip protects that portion of the impregnated gauze it covers from contamination. The first protective strip 12 includes a second leg 12D which, as will be explained, folds over a portion of the second protective strip.

The first protective strip 12 further includes a third leg 12E which can be folded so as to provide a small tab which can be grasped by the fingers of the user.

As embodied, the second protective strip 14 consists of a first leg 14A which is in engagement with the adhesive surface 6 of the backing 4 in the same fashion as leg 12B of the first protective strip 12.

The second leg 14B of the second protective strip is positioned between the absorbent pad 8 and the sheet of impregnated gauze 10 and includes a portion 14E extending beyond the absorbent pad into contact with the adhesive surface of the backing. The function of the second leg 14B is to separate the impregnated gauze 10 and the absorbent pad 8 until the impregnated bandage is ready for use.

The first 14A and second 14B legs of the second protective strip come together to form a double layered third leg 14C which is adapted to fold over into superimposed relationship with the upper surface of the impregnated sheet of gauze. The third leg 14C extends to a fourth leg which can include a tab 14D which can be grasped by the finger of the user. FIG. 2 shows the impregnated bandage of this invention in its folded condition prior to use. The folded bandage of FIG. 2, it will be understood, can be placed within a sterilized package.

In accordance with this invention there is a preferred method of procedure for assembling the impregnated bandage of this invention, although production of the dressing is not limited to this method.

The preferred method or procedure for assembling the impregnated bandage of this invention is illustrated in FIGS. 3–7.

In FIG. 3 there is shown the step of applying or attaching the pad 8 made up of absorbent material so that it is evenly spaced from the longitudinal edges of the backing strip 2. The absorbent pad 8 is, of course, maintained in its desired position by the adhesive portion 6 of the backing strip 2. Although as shown the absorbent pad 8 is spaced from the lengthwise edges of the backing strip, the invention is not limited to such construction. In some embodiments the absorbent pad and the backing strip may be flush with one another. In other words, in some embodiments the width of the absorbent pad and the backing strip are the same.

The next step in the operation is to attach the second protective strip as shown in FIG. 4. Thus the leg 14B of the second protective strip is placed in face-to-face superimposed relationship with the absorbent pad 8.

The leg 14B includes an extension 14E which is attached to the adhesive surface 6A of the backing strip. The extension 14E is relatively small so that it is possible to detach the extension 14E from the adhesive surface 6 with a relatively small pulling force. Alternatively, the backing strip can be constructed so that there is a narrow area 6A where there is no adhesive and the backing surface is plain. This embodiment makes it much easier to remove the protective strip when the impregnated bandage is ready for use.

The other leg 14A of the second protective strip is placed in engagement with the adhesive surface 6A of the backing strip 2 to cover the same prior to use. As can be seen the leg 14C of the second protective strip is, at this time, in a tilted position from the vertical position but is moving towards the vertical position.

Figure 5:
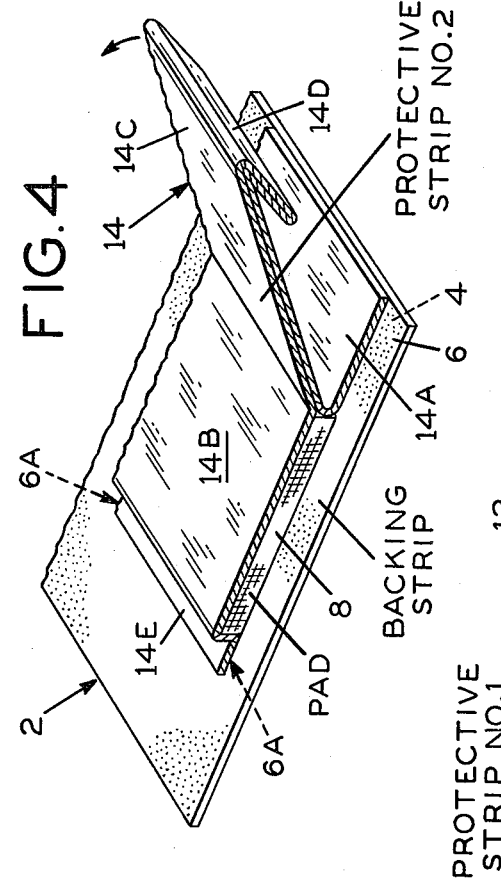
FIG. 5 is a drawing of the invention similar to FIG. 4 with the gauze layer to be impregnated added.

FIG. 5 shows the assembly process following the addition of the gauze sheet 10. The gauze sheet 10 at this stage may have previously been impregnated with the impregnant or alternatively the impregnant may be added subsequent to the assembly of the gauze. This is largely a matter of manufacturing convenience.

The gauze sheet 10 includes extension 10B which overlies extension 14E of the second protective strip, and extension 10A which is in superimposed face-to-face relationship with the adhesive surface 6A of the backing strip 2. The leg 14C of the second protective strip is in essentially a vertical position at this time.

Figure 6:
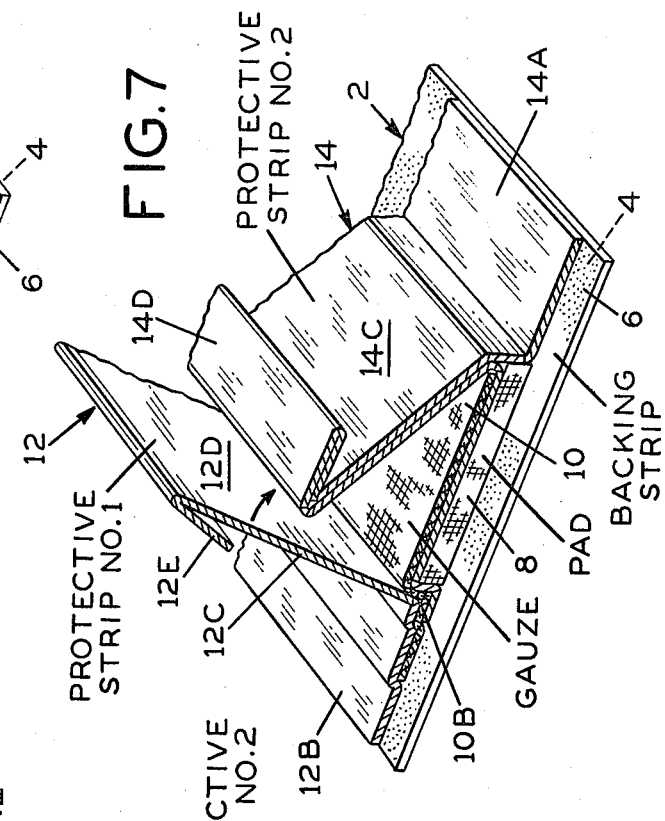
FIG. 6 is a drawing of the invention similar to FIG. 5 with a protective strip No. 1 added.
Figure 7:
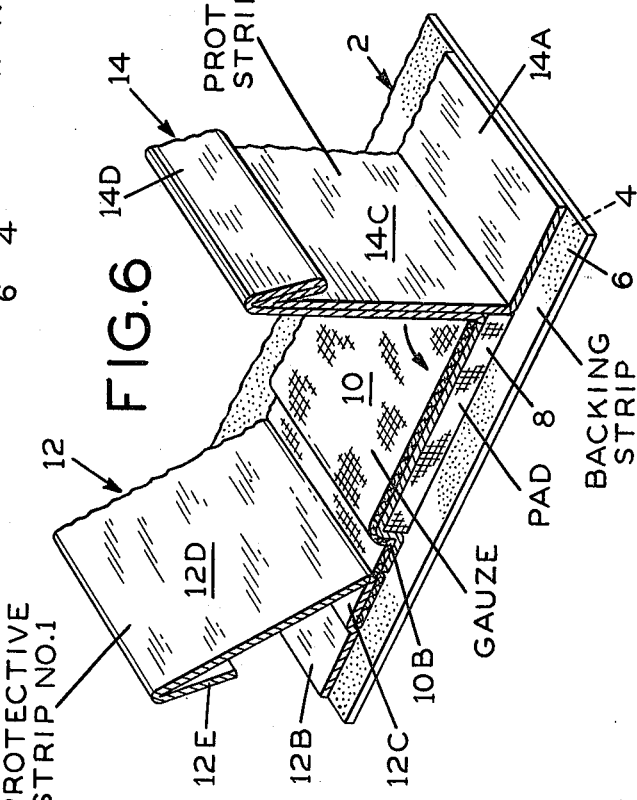
FIG. 7 is a drawing of the invention similar to FIG. 6 with the protective strips canted towards each other prior to final assembly.

In FIG. 6 the first protective strip 12 has been added so that portion 12B is in engagement with the adhesive surface 6A and portion 12 is in face-to-face relationship with the extension 10A of the gauze sheet 10. FIG. 7 shows the legs 14C of the second protective strip and 12D of the first protective strip being folded in the direction shown by the arrows in that figure. The protective strips are folded until in the position of FIG. 2 which is the fully assembled position of the impregnated bandage.

FIG. 7 shows the impregnated bandage structure being folded towards the completely folded position of FIG. 2.

The impregnated bandage of this invention is applied as follows.

The impregnated bandage in the form shown in FIG. 2 is brought to the wound and positioned so that the protective strips face the wound area. The gripping flap 12E is engaged and moved in the direction of the arrow in FIG. 2. This causes the leg 12D of the first protective strip to uncover the legs 14C and 14D of the second protective strip. The gripping leg or flap 14D is then grasped. A pulling force is then applied to the gripping legs or flaps 12E and 14D with the leg 14B posed above the wound.

Continued pulling force on the gripping flaps 12E and 14D will cause the leg 14B which is sandwiched between the impregnated gauze sheet 10 and the absorbent pad 8 to slide from this position so that the absorbent pad and impregnated gauze sheet can come into face-to-face contact and so that the impregnated gauze sheet 10 is face-to-face with the wound. Pressure is then placed on this portion of the bandage to bring it into firm contact with the wound. As the pulling force continues leg 14A of the second protective strip 14 and leg 12A of the first protective strip will uncover the adhesive surfaces 6 on the backing strip 2. These adhesive surfaces are placed in engagement with the skin of the patient adjacent the wound to hold the impregnated bandage in position.

What is claimed is:
1. An impregnated bandage comprising:
(a) a backing having an adhesive surface on one side;
(b) an absorbent pad positioned partially along the length and intermediate the ends of the adhesive strip;
(c) a first protective strip attached to one portion of the adhesive extending beyond one end of the absorbent pad;
(d) a second protective strip having a first leg connected to a second portion of the adhesive extending beyond the other end of the absorbent pad;
(e) said second protective strip having a second leg positioned on the top of the absorbent pad;
(f) an impregnated gauze strip positioned in face-to-face engagement with the upper surface of said second leg of said second protective strip.
2. An impregnated bandage comprising:
(a) a backing having an adhesive surface;
(b) an absorbent pad positioned on the adhesive surface of said backing intermediate the ends thereof;
(c) an impregnated absorbent gauze superimposed over said absorbent pad;
(d) a protective strip positioned between said absorbent pad and said impregnated gauze sheet to thereby prevent contact between said absorbent pad and said impregnated absorbent sheet until said protective paper is removed.
3. An impregnated bandage comprising:
(a) a backing strip having one adhesive surface;
(b) an absorbent pad positioned on the adhesive surface of the backing strip intermediate the ends thereof so that there are adhesive surfaces adjacent the terminal edge of said absorbent pad adapted to engage the body adjacent the wound;

(c) an impregnated gauze sheet superimposed on said absorbent pad;

(d) a first and a second protective strip, said protective strips including a portion positioned in sandwich-like relationship between said absorbent pad and said impregnated gauze strip and including portions which protect the adhesive surfaces adjacent said absorbent pad prior to use of the bandage; and (e) means for sliding that portion of the protective strip from the position between said absorbent pad and said impregnated gauze sheet and for removing the protective strips from the adhesive surfaces so that the impregnated bandage can be applied.

4. An impregnated bandage as defined in claim 3 wherein said first protective strip includes a leg means releasably attached to said adhesive surface of said backing strip on one side of said absorbent pad.

5. An impregnated bandage as defined in claim 4 wherein said second protective strip includes a first leg means releasably attached to said adhesive surface of said backing strip at the other end of said absorbent pad and a second leg means comprising a first layer of said second protective strip positioned between said absorbent pad and said impregnated gauze sheet.

6. An impregnated bandage as defined in claim 5 wherein extensions of said first and said second legs of said second protective strip form together a third leg comprising a double layer of protective strips in superimposed relationship with said impregnated gauze sheet.

7. An impregnated bandage as defined in claim 6 wherein said double layer of said protective strip is bent backwards and is adapted to form another layer of release paper in face-to-face relationship with said impregnated gauze sheet and to provide a gripping tab.

8. An impregnated bandage as defined in claim 7 wherein said first leg of said protective strip is attached to a second leg means adapted to be placed in sandwich-like relationship with said gripping tab and said second layer of said second protective strip.

9. An impregnated bandage as defined in claim 8 wherein said second leg means of said first protective strip has a reverse portion forming a gripping tab.

10. An impregnated bandage as defined in claim 9 wherein said absorbent gauze sheet is impregnated with a medicinal composition.

11. An impregnated bandage as defined in claim 9 wherein said absorbent gauze sheet is impregnated with a petroleum composition.

12. A bandage adapted to cover a wound and be attached to the human body comprising:

(a) a backing strip one surface of which is coated with an adhesive;

(b) an absorbent pad attached to the adhesive surface of said backing strip so that there are first and second end portions of said backing strip adhesively coated and adapted to be connected to the body;

(c) an impregnated gauze sheet on said absorbent pad, said impregnated gauze sheet having a portion in engagement with the adhesive surface of said backing strip;

(d) protective strip means having portions engaging the first and second end portions of said backing strip, and a portion positioned between said absorbent pad and said impregnated gauze sheet to prevent wicking of the impregnant into said absorbent pad, said protective strip means being removable prior to the application of the bandage to the wound.

13. A bandage as defined in claim 12 wherein said protective strip means comprise first and second protective strips.

14. A bandage as defined in claim 13 wherein said first protective strip has a leg portion adapted to engage one of said end portions of said backing strip.

15. A bandage as defined in claim 14 wherein said second protective strip has one leg portion adapted to engage said other end portion of said backing strip and another leg portion positioned between said absorbent pad and said impregnated gauze sheet.

16. A bandage as defined in claim 15 wherein said first and said second protective strips have means for gripping said strips so that by a pulling force said protective strips are removed from engagement with said adhesive surfaces on said backing strip.

17. A bandage as described in claim 16 wherein said gripping means comprises tabs on the free ends of said first and second protective strips.

18. A bandage comprising:

(a) a first wound contacting impregnated gauze layer;

(b) a second secretion absorbing pad layer above said contacting impregnated gauze layer;

(c) a backing strip having an adhesive surface in engagement with said pad layer;

(d) said first wound contacting layer having a portion in engagement with said adhesive surface;

(e) said first and second layers being positioned on said backing strip so as to provide first and second adhesive end portions;

(f) protective strip means for protecting said first and second end portions and for separating said contacting impregnated layer and said pad layer until immediately prior to use;

(g) said protective strip means being removed while said bandage is applied to the wound.

19. A method of assembling an impregnated bandage comprising:

(a) providing a backing strip having an adhesive coating on one side;

(b) placing an absorbent pad on the adhesive side of said backing strip so that the free ends of the adhesive surface can be attached to the body;

(c) placing the first leg of a protective strip in face-to-face relationship with the upper surface of the absorbent pad;

(d) placing the second leg of the protective strip in face-to-face relationship with one of the free ends of said adhesive surface, there being a third free leg;

(e) placing a sheet of gauze in superimposed face-to-face relationship with the leg of the protective strip in engagement with the upper surface of the absorbent pad, a portion of said sheet of gauze being in engagement with said adhesive coating;

(f) placing the first leg of another protective strip in face-to-face relationship with the other adhesive surface of the backing strip, there being a second free leg;

(g) folding said free legs of said protective strips so that the third leg is in superimposed face-to-face relationship with said gauze strip, and said second free leg is in superimposed face-to-face relationship with said third leg.

20. A method of forming an impregnated bandage comprising:
 (a) providing a backing sheet having an adhesive coating on one side;
 (b) placing an absorbent pad in engagement with the adhesive surface of an adhesive backing in a position so that there are two free adhesive surfaces on opposite sides of said absorbent pad;
 (c) placing leg means of first and second protective strips in engagement with the free adhesive surfaces of said backing sheet;
 (d) placing another leg means of one of said protective strips in superimposed face-to-face relationship with the upper surface of said absorbent pad;
 (e) positioning an impregnated gauze sheet in superimposed face-to-face relationship with the leg of the protective strip in paragraph (d) above;
 (f) folding free legs of said protective strip in superimposed relationship so as to cover the upper surface of said gauze sheet.

21. A method of applying to the wound on a human body an impregnated bandage having an absorbent pad positioned on the adhesive surface of a backing strip between the ends thereof so that there are terminal adhesive end positions and said bandage having first and second protective strips attached to the terminal adhesive surfaces of said protective strips and one of said release papers including a leg positioned in superimposed face-to-face relationship with said absorbent pad, said bandage further having an impregnated gauze sheet in superimposed face-to-face relationship with the protective strip leg in engagement with said absorbent pad comprising:
 (a) positioning said impregnated bandage adjacent the wound;
 (b) grasping the free ends of said protective strips and moving them to uncover said impregnated gauze sheet;
 (c) applying pulling force to said free ends of the protective strips so that said impregnated gauze is exposed and then brought in engagement with the wound;
 (d) applying continuing pulling force to said free ends of said protective strips so as to uncover the free adhesive portions of said backing strip and to slidably remove leg of said protective strip positioned between said absorbent pad and said impregnated gauze sheet so that said impregnated gauze sheet can contact said absorbent pad;
 (e) placing said free adhesive portions of said backing strip in adhering engagement with the portion of the body adjacent the wound.

22. A method of assembling an impregnated bandage comprising:
 (a) providing a backing sheet with one adhesive surface;
 (b) providing an absorbent pad of sufficient size to absorb wound secretions and placing the same in engagement with the adhesive surface of said backing strip so that the backing strip has free end portions the adhesive surfaces of which can be used to attach the bandage to the wound.
 (c) providing a protective strip and placing one leg of said protective strip in engagement with one of the free ends of said adhesive surfaces and another leg in face-to-face engagement with said absorbent pad;
 (d) providing a gauze strip causing said strip to become impregnated with a suitable impregnant;
 (e) placing said impregnated gauze sheet in face-to-face engagement with the other leg of said protective strip and placing a small portion of said impregnated gauze strip in engagement with one of said adhesive surfaces adjacent said absorbent pad;
 (f) providing another protective strip and placing one leg of said protective strip in engagement with the other free adhesive surface of said backing strip.

* * * * *

UNITED STATES PATENT AND TRADEMARK OFFICE
CERTIFICATE OF CORRECTION

PATENT NO. : 4,176,664
DATED : December 4, 1979
INVENTOR(S) : Stanley Kalish

It is certified that error appears in the above—identified patent and that said Letters Patent is hereby corrected as shown below:

Column 5, line 68, "from" should read -- for --.

Signed and Sealed this

Fifteenth Day of April 1980

[SEAL]

Attest:

Attesting Officer

SIDNEY A. DIAMOND

Commissioner of Patents and Trademarks